(12) United States Patent
West et al.

(10) Patent No.: US 6,169,193 B1
(45) Date of Patent: Jan. 2, 2001

(54) POLYSILOLES AND POLYGERMOLES

(75) Inventors: Robert C. West, Madison, WI (US); Honglae Sohn, San Diego, CA (US); Yuxia Liu, Madison, WI (US)

(73) Assignee: Wisconsin Alumni Research Foundation, Madison, WI (US)

( * ) Notice: Under 35 U.S.C. 154(b), the term of this patent shall be extended for 0 days.

(21) Appl. No.: 09/490,573

(22) Filed: Jan. 25, 2000

Related U.S. Application Data

(60) Provisional application No. 60/117,628, filed on Jan. 28, 1999.

(51) Int. Cl.$^7$ .......................................... C07F 7/08
(52) U.S. Cl. ................. 556/406; 556/9; 556/87; 556/95
(58) Field of Search ................. 556/406, 9, 87, 556/95

(56) References Cited

U.S. PATENT DOCUMENTS

| | | | |
|---|---|---|---|
| 5,412,105 | * 5/1995 | Ito et al. ........................ | 556/406 X |
| 5,498,736 | * 3/1996 | Tamao et al. ..................... | 556/406 |
| 5,741,921 | * 4/1998 | Kreuder et al. ................... | 556/406 |

OTHER PUBLICATIONS

T. Sanji et al., Silole–Incorporated Polysilanes, 120 J.Am. Chem. Soc. 4552–4553 (1998).
Yamguchi et al., Silicon–Catenated Silole Oligomers: Oligo(1,1–silole)s, 16 Organometallics 2486–2488 (1997).
W. Joo et al., Synthesis and reactivity of 1,1–disodio–2,3, 4,5–tetraphenyl–1–silacyclopentadiene, 391 J. Organomet. Chem. 27–36 (1990).
R. West et al., The Dianion of Tetraphenylgermole is Aromatic, 36 Angewandte Chemie Int. Ed. Engl. 1002–1004 (1996).

* cited by examiner

*Primary Examiner*—Paul F. Shaver
(74) *Attorney, Agent, or Firm*—Quarles & Brady

(57) ABSTRACT

Disclosed herein are polysilole and polygermole compounds. The silicon or germanium ring atom is directly linked in the polymer to another silicon or germanium ring atom from another polymer unit. The result is compounds that fluoresce and have electroluminescence. Coupling reactions to form such compounds are also disclosed.

10 Claims, 1 Drawing Sheet

POLYSILOLES AND POLYGERMOLES

CROSS-REFERENCE TO RELATED APPLICATION

This application claims priority based on U.S. provisional application Ser. No. 60/117,628, filed on Jan. 28, 1999.

STATEMENT REGARDING FEDERALLY SPONSORED RESEARCH

This invention was made with United States government support awarded by the following agency: NSF 9531155. The United States has certain rights in this invention.

BACKGROUND OF INVENTION

The present invention relates to derivatives of siloles and germoles which have desirable electronic properties. More particularly, it relates to polysiloles, polygermoles, and silole-germole copolymers.

Siloles are compounds having a 5-member ring in which there are four carbons in the ring and one silicon. There are also two double bonds not involving the silicon. The ring may be substituted (or not) insofar as the carbon atoms are concerned, and the silicon is linked to two adjacent ring carbons. Typically, the silicon is also linked to two other atoms outside the ring (e.g. halogens). Germoles are similar except that germanium substitutes for silicon in the ring.

Siloles and germoles are of considerable commercial interest because of their unusual electronic properties. In particular, it has been proposed that they be used for electro-transporting materials and light-emitting diodes.

Recently, silole-polysilane copolymers were reported where single silole units were linked to a standard polysilane moiety, that moiety in turn being the repeat unit of the polymer. See generally T. Sanji et al., 120 J. Am. Chem. Soc. 4552–4553 (1998). The disclosure of this publication and of all other publications referred to herein are incorporated by reference as if fully set forth herein.

Also, there was a recent report of the synthesis of a four repeat silole oligomer. See Yamaguchi et al., 16 Organometalics 2486–2488 (1997). However, such oligomers do not have desirable film forming properties, or certain desired electrical properties. This greatly limits their utility.

There is therefore a continuing desire to develop additional compounds having varied electrical properties, particularly with respect to fluorescence, electroluminescence, and semiconducting.

BRIEF SUMMARY OF THE INVENTION

In one aspect, the invention provides compounds containing the following moiety:

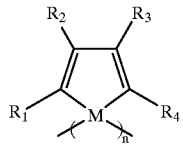

wherein M is selected from the group consisting of silicon and germanium; n is at least five (preferably less than 10,000, even more preferably less than 500, most preferably between 8 and 100); and $R_1$, $R_2$, $R_3$, and $R_4$ are for each of the n's individually selected from the group consisting of hydrogen, fluorine, alkyl having less than 30 carbons, alkoxy having less than 30 carbons, alkyl silyl having less than 30 carbons, arylalkyl having less than 30 carbons, and aryl having less than 30 carbons.

Most preferably, all $R_1$, $R_2$, $R_3$, and $R_4$ are aryl, such as substituted or unsubstituted phenyl. For some applications, it is preferred that the compound be a homopolymer of such moieties, or a compound whose molecular weight is at least 90% from such moieties. In using the term homopolymer it should be understood that the term is meant to include polymers in which the units are identical except that in the terminal units the Si (or Ge) will be linked to some form of terminal group or atom (e.g. halogen, o-alkyl).

In one form, M is silicon for all n's. In another, M is germanium for all n's. In still another, M is silicon for at least one n and germanium for at least one n (e.g. they alternate).

In another aspect the invention provides a method of making the above compounds. One reacts dianions of one or more compounds selected from the group consisting of siloles and germoles, and/or salts thereof, with one or more compositions selected from the group consisting of dihalogenated siloles and dihalogenated germoles (in each case the dihalogenation referring to substitution on silicon or germanium). The overall conditions of the reaction are effective to cause a polymerization reaction (heat over 50° C., preferably over 125° C.).

In yet another aspect, the invention provides an alternative method of making the above compounds. One reduces a plurality of units of one or more chemicals selected from the group consisting of dihalogenated siloles and dihalogenated germoles (in each case the dihalogenation referring to substitution on silicon or germanium) using a material selected from the group consisting of lithium metal, sodium metal, and potassium metal. The reduced units are then coupled at a reaction condition above 50° C., preferably above 125° C.

Compounds made by the above methods have been determined to have important electrical properties. They are fluorescent and have shown electroluminescent properties. They should be particularly useful in organic transistors, in contexts where electron transporting materials are desired, and for single compound LED's for flat panel displays.

The objects of the present invention therefore include providing:

(a) compounds of the above kind which are fluorescent;
(b) compounds of the above kind which are electroluminescent; and
(c) efficient methods of making such compounds.

These and still other objects and advantages of the present invention (e.g. room temperature stability) will be apparent from the description which follows. The following description is merely of the preferred embodiments. The claims should therefore be looked to in order to understand the full scope of the invention.

DETAILED DESCRIPTION OF THE INVENTION

Example 1

Figure 1:
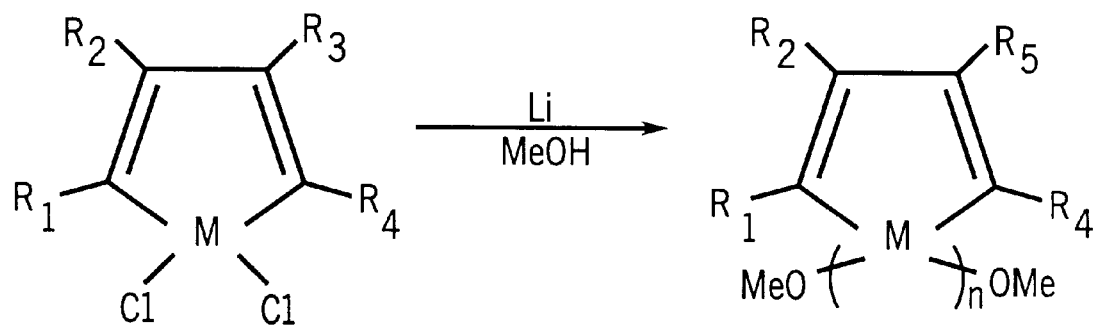
FIG. 1 is a schematic depiction of a polymerization reaction of the present invention.
Figure 2:
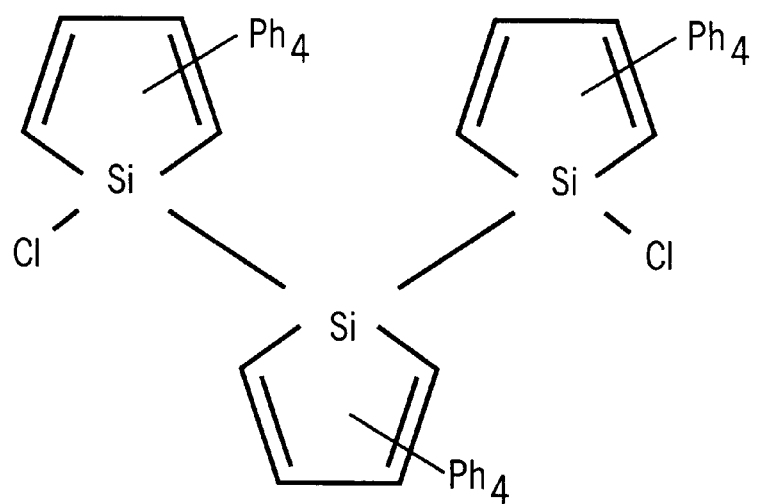
FIG. 2 is a schematic depiction of an intermediate polysilole.

Preparation of poly(2,3,4,5-tetraphenylsilole) polymer by reaction of 2,3,4,5-tetraphenylsilole dianion with 1,1- dichloro-2,3,4,5-tetraphenylsilole in solid phase. A 250 mL schlenk flask with a magnetic stirrer was flame-dried under vacuum and connected to an argon inlet. 1,1-Dichloro-2,3,4,5-tetraphenylsilole (see generally W. Joo et al., 391 J. Organomet. Chem. 27–36 (1990)) (1.00 g, 2.20 mmol), Li metal (0.10 g, 14.3 mmol) and THF (30 mL) were introduced and stirred at room temperature for 12 hours.

The mixture turned to dark purple and the silole dianion was formed. Another 250 mL schlenk flask with a magnetic stirrer was flame-dried under vacuum and connected to an argon inlet. (1.00 g, 2.20 mmol) of the dichloro compound and THF (50 mL) was introduced and stirred about 10 min. The second flask was cooled to −78° C., then the silole dianion solution in the first flask was introduced by cannulation. THF was removed by evaporating under vacuum at 0° C. and the resulting dark solid was heated to 150° C. for three days. The color of the solid changed to yellow after two days.

The flask cooled to room temperature and toluene (150 mL) was added. The resulting solution was washed with distilled water to remove salts, then filtered to remove a small amount of insoluble residue. The solution was concentrated to 20 mL by evaporating the solvent. The polymer was precipitated by slow addition of 500 mL of methanol, separated by filtration and dried under vacuum at 100° C. overnight. The obtained polymer was a bright yellow solid with a yield of 100%, average molecular weight ($M_w$) of 5900, and a PDI of 1.14.

While lithium was used in the above example, an equivalent amount of sodium or potassium metal would also suffice.

Example 2

Preparation of poly(2,3,4,5-tetraphenylgermole) polymer by reaction of 2,3,4,5-tetraphenylgermole dianion with 1,1-dichloro-2,3,4,5-tetraphenylgermole in solid phase. A 250 mL schlenk flask with a magnetic stirrer was flame-dried under vacuum and connected to an argon inlet. 1,1-dichloro-2,3,4,5-tetraphenylgermole (see generally West et al., 36 Angewandte Chemie Int. Ed. Engl. 1002–1004 (1996)) (1.50 g, 3.00 mmol), Li metal (94.5 mg, 13.5 mmol) and THF (40 mL) were introduced and stirred at room temperature for 12 hours.

The mixture turned to dark purple and the germole dianion was formed. Another 250 mL schlenk flask with a magnetic stirrer was flame-dried under vacuum and connected to an argon inlet. (1.50 g, 3.00 mmol) of the dichloro compound and THF (50 mL) was introduced and stirred about 15 min. The second flask was cooled to −78° C., then the germole dianion solution in the first flask was introduced by cannulation. THF was removed by evaporating under vacuum at 0° C. and the resulting dark solid was heated to 170° C. for a week. The color of the solid changed to brown.

The flask cooled to room temperature and toluene (150 mL) was added. The resulting solution was washed with distilled water to remove salts, then filtered to remove a small amount of insoluble residue. The solution was concentrated to 20 mL by evaporating the solvent. The polymer was precipitated by slow addition of 500 mL of methanol, separated by filtration and dried under vacuum at 100° C. overnight. The obtained polymer was a bright yellow solid with a yield of 88%, average molecular weight ($M_w$) of 1800, and a PDI of 1.44.

Example 3

Preparation of poly(2,3,4,5-tetraphenylgermole-2,3,4,5-tetraphenylsilole) alternating copolymer by reaction of 2,3,4,5-tetraphenylgermole dianion with 1,1-dichloro-2,3,4,5-tetraphenylsilole in solid phase. A 250 mL schlenk flask with a magnetic stirrer was flame-dried under vacuum and connected to an argon inlet. 1,1-dichloro-2,3,4,5-tetraphenylgermole (1.00 g, 200 mmol), Li metal (62.5 mg, 9.0 mmol) and THF (50 mL) were introduced and stirred at room temperature for 36 hours.

The mixture turned to dark purple and the germole dianion was formed. Another 250 mL schlenk flask with a magnetic stirrer was flame-dried under vacuum and connected to an argon inlet. 1,1-dichloro-2,3,4,5-tetraphenylsilole (0.91 g, 2.00 mmol) and THF (50 mL) was introduced and stirred about 15 min. The second flask was cooled to −78° C., then the germole dianion solution in the first flask was introduced by cannulation. THF was removed by evaporating under vacuum at 0° C. and the resulting dark solid was heated to 170° C. for a week. The color of the solid changed to brown.

The flask cooled to room temperature and toluene (150 mL) was added. The resulting solution was washed with distilled water to remove salts, then filtered to remove a small amount of insoluble residue. The solution was concentrated to 20 mL by evaporating the solvent. The copolymer was precipitated by slow addition of 500 mL of methanol, separated by filtration and dried under vacuum at 100° C. overnight. The obtained copolymer was a bright yellow solid with a yield of 76%, average molecular weight ($M_w$) of 3200, and a PDI of 1.37.

Example 4

Preparation of poly(2,3,4,5-tetraphenylsilole) polymer from 1,1-dichloro-2,3,4,5-tetraphenylsilole using reduction coupling. A 250 mL 3-neck flask was equipped with a condenser connected to an argon inlet, a mechanic stirrer and a 100 mL pressure-equalized dropping funnel. 1,1-dichloro-2,3,4,5-tetraphenylsilole (2.33 g, 5.11 mmol), Na metal (0.29 g, 12.6 mmol) and toluene (40 mL) were mixed and refluxed at 110° C. for 4 hours. The mixture turned red from green during the reaction. Me$_2$PhSiCl (1.86 g. 10.1 mmol) was then added from the dropping funnel in less than a minute. The reaction continued for 3 hours under toluene reflux.

The mixture was then cooled to room temperature and quenched with 10 mL of methanol. Toluene (100 mL) was added to dilute the solution, and the mixture was washed with distilled water to remove salts, then filtered to remove a small amount of insoluble residue. The toluene solution was concentrated to 30 mL by evaporating some solvent. The polymer was precipitated from this solution by slow addition of 500 mL of methanol, separated by filtration and dried under vacuum at 80° C. for 2 hours. The polymer was a bright yellow solid and the yield was 1.15 g (58.5%). It was soluble in acetone, THF and toluene, partially soluble in hexane, and insoluble in isopropanol, methanol and water. Selected data for the polymer: $M_w$=3800, PDI=1.02, $^1$H NMR (300.133 Mhz, CDCl$_3$): δ=5.95–7.85 (br, 20H, pH); $^{13}$C{H} NMR (75.403 Mhz, CDCl$_3$): δ=125–138 (br); Solid State $^{29}$Si NMR: δ=6.940; UV (in THF) $\lambda_{max}$=364 nm, tails to 500 nm; Fluorescence (emission, in THF) $\lambda_{max}$=520 nm.

It should be appreciated that while the above examples focus on phenyl substituted siloles and germoles (and the corresponding polymers) the invention is not so limited. In this regard, hydrogen, fluorine, branched and unbranched alkyl groups having less than 30 carbons (preferably methyl and ethyl), alkoxy groups having less than 30 carbons (such as methoxy), alkyl silyl groups having less than 30 carbons (such as trimethyl silyl), aryl groups having less than 30 carbons, and arylalkyl groups having less than 30 carbons can be substituted for the phenyl groups using similar techniques. Obtaining corresponding monomer starting materials for such purposes is well within the skill of the art.

Moreover, while the present examples are of homopolymers that are terminated with halogen and/or o-alkyl groups such as o-methyl, the nature of the moiety terminus is not critical, and the terminal units may even be linked to each other so as to form a ring. Further, while n averaging around 15 is preferred, for various applications significantly higher n's may be desirable.

Thus, the invention is not to be limited to the specific examples listed above. Rather, protection should be given to the full scope of the invention.

Industrial Applicability

The present invention provides compounds useful for various electrical purposes such as LED displays, and efficient methods for producing them.

We claim:

1. A compound having the following moiety:

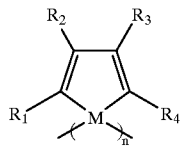

wherein M is selected from the group consisting of silicon and germanium; n is at least five, and $R_1$, $R_2$, $R_3$, and $R_4$ are for each of the n's individually selected from the group consisting of hydrogen, fluorine, alkyl having less than 30 carbons, alkoxy having less than 30 carbons, alkyl silyl having less than 30 carbons, arylalkyl having less than 30 carbons, and aryl having less than 30 carbons.

2. The compound of claim 1, wherein n is less than 10,000.

3. The method of claim 2, wherein M is silicon and each of $R_1$, R2, $R_3$, and $R_4$ are phenyl.

4. The compound of claim 2, wherein the compound is a homopolymer of such moieties.

5. The compound of claim 2, wherein all of $R_1$, $R_2$, $R_3$, and $R_4$ in each case are aryl.

6. The compound of claim 2, wherein M is silicon for all n's.

7. The compound of claim 2, wherein M is germanium for all n's.

8. The compound of claim 2, wherein M is silicon for at least one n and germanium for at least one n.

9. A method of making the compound of claim 2, comprising:

at a temperature in excess of 50° C. reacting dianions of one or more chemicals selected from the group consisting of siloles and germoles, and/or salts thereof, with one or more compositions selected from the group consisting of dihalogenated siloles and dihalogenated germoles (in each case said dihalogenation referring to substitution on the silicon or germanium).

10. A method of making the compound of claim 2, comprising:

reducing a plurality of units of chemicals selected from the group consisting of dihalogenated siloles and dihalogenated germoles (in each case said dihalogenation referring to substitution on the silicon or germanium), with a material selected from the group consisting of lithium metal, sodium metal, and potassium metal; and thereafter coupling the reduced units together at a temperature in excess of 50° C.

* * * * *